(12) United States Patent
Koglin

(10) Patent No.: US 11,890,215 B2
(45) Date of Patent: Feb. 6, 2024

(54) DEVICE AND METHOD TO ASSIST WITH APPLYING A SLEEVE TO APPENDAGES

(71) Applicant: Iowa Strength Supply LLC, Redfield, IA (US)

(72) Inventor: Joshua P. Koglin, Redfield, IA (US)

(73) Assignee: IOWA STRENGTH SUPPLY LLC, Redfield, IA (US)

( * ) Notice: Subject to any disclaimer, the term of this patent is extended or adjusted under 35 U.S.C. 154(b) by 860 days.

(21) Appl. No.: 16/944,308

(22) Filed: Jul. 31, 2020

(65) Prior Publication Data
US 2021/0038416 A1 Feb. 11, 2021

Related U.S. Application Data

(60) Provisional application No. 62/885,004, filed on Aug. 9, 2019.

(51) Int. Cl.
*A61F 5/01* (2006.01)
*A41D 13/06* (2006.01)

(52) U.S. Cl.
CPC .......... *A61F 5/0109* (2013.01); *A41D 13/065* (2013.01); *A41D 2400/44* (2013.01)

(58) Field of Classification Search
CPC ....... A61F 5/0102–0111; A61F 5/0118; A41D 13/065; A41D 13/06; A41D 13/08; A41D 13/0568; A41D 2400/44; A41D 2400/70; A41D 2400/80; A41D 2400/82; A41D 17/00; A41D 17/005; A41D 17/02; A41D 27/10; A41D 27/22; A41D 2300/33; A41D 2300/332
See application file for complete search history.

(56) References Cited

U.S. PATENT DOCUMENTS 3,703,728 A * 11/1972 Saunders .................. F41B 5/14
2/16
D330,505 S * 10/1992 Doyle ........................... D8/356
(Continued)

FOREIGN PATENT DOCUMENTS

KR 101784075 B1 10/2017

OTHER PUBLICATIONS

McDavid, "Knee Brace", Apr. 22, 2016, https://www.overstock.com/Health-Beauty/McDavid-Classic-429-Level-3-Knee-Brace-with-Polycentric-Hinges-Black/11368305/product.html.
(Continued)

*Primary Examiner* — Ismael Izaguirre
(74) *Attorney, Agent, or Firm* — Goodhue, Coleman & Owens, P.C.

(57) ABSTRACT

An apparatus for applying a support/compression sleeve in embodiments of the present disclosure may have one or more of the following features: (a) a first sleeve applicator body for placement between the sleeve and a user's body, (b) an upper strap extending from upper strap receptors located at an upper portion of the first sleeve applicator body, (c) a lower strap extending from lower strap receptors located at a lower portion of the first sleeve applicator body, (d) a second sleeve applicator body for placement between the sleeve and the user's body, (e) an upper strap extending from upper strap receptors located at an upper portion of the second sleeve applicator body, and (f) a lower strap extending from lower strap receptors located at a lower portion of the second sleeve applicator body.

11 Claims, 14 Drawing Sheets

(56) References Cited

U.S. PATENT DOCUMENTS

| | | | | |
|---|---|---|---|---|
| 5,405,312 A * | 4/1995 | Jacobs | ............... | A41D 13/0568 |
| | | | | 128/892 |
| 5,625,896 A * | 5/1997 | LaBarbera | ......... | A63B 71/1225 |
| | | | | 2/22 |
| 6,063,048 A | 5/2000 | Bodenschatz et al. | | |
| 6,098,933 A * | 8/2000 | Stein | ..................... | B65F 1/1415 |
| | | | | D9/434 |
| 6,447,037 B1 * | 9/2002 | Crouch | .................. | B65D 33/14 |
| | | | | 294/149 |
| 6,598,769 B1 * | 7/2003 | Franco | ................. | A47G 25/905 |
| | | | | 223/118 |
| 8,911,389 B2 | 12/2014 | Reinhardt et al. | | |
| 9,814,341 B2 * | 11/2017 | Kobyluck | .............. | A47G 25/90 |
| 10,159,588 B1 | 12/2018 | Nelson | | |
| 2007/0060857 A1 | 3/2007 | Testa | | |
| 2007/0149368 A1 | 6/2007 | Koch | | |
| 2010/0078450 A1 * | 4/2010 | Longhurst | .............. | A47G 25/90 |
| | | | | 223/111 |
| 2017/0216124 A1 | 8/2017 | Kaneyama | | |

OTHER PUBLICATIONS

Mmar Medical, "Hely Weber Axis Hinged Knee Sleeve", Jul. 5, 2010, https://www.mmarmedical.com/Hely-Weber-Axis-Hinged-Knee-Sleeve-p/3655xs-3755xxl.htm.

* cited by examiner

DEVICE AND METHOD TO ASSIST WITH APPLYING A SLEEVE TO APPENDAGES

CROSS-REFERENCE TO RELATED APPLICATIONS

This application claims priority under 35 U.S.C. § 119 to provisional application Ser. No. 62/885,004 filed Aug. 9, 2019, which is incorporated by reference in its entirety.

FIELD OF THE INVENTION

The present disclosure relates to compression sleeves, such as orthopedic or sports sleeves. Particularly, the present disclosure relates to sleeves for bodily appendages, such as the elbow or knee. More particularly, but not exclusively, the present disclosure relates to a device for applying a sleeve to an elbow or knee of a user.

BACKGROUND

Raw powerlifting means lifting and competing with little or no additional equipment. Generally, the only approved equipment in raw meets are approved: singlets, lifting belts, wrist wraps, knee sleeves and chalk.

The reason for the division of raw lifting vs. equipped lifting has come about due to people arguing equipment will allow more weight to be lifted. More weight can be lifted by the same person with the extra equipment than he/she could without it. In fact, research indicates using powerlifting equipment might help the lifters lift 115% more than without.

Most all rule books for raw powerlifting include the use of neoprene knee sleeves. USA Powerlifting Raw/Unequipped Standards allow single-ply neoprene knee sleeves without attaching and/or tightening mechanisms like Velcro, clips, or straps. IPF Rules for CLASSIC (raw/unequipped) Lifting allows for sleeves, being cylinders of neoprene, may be worn only on the knees by the lifter in the performance of any lift in competition; sleeves cannot be worn or used on any part of the body other than the knees Knee sleeves keep the knee joints warm and flexible, thus, keeping injury and soreness to a minimum. But when it comes to powerlifting, most lifters wear them a couple of sizes too small in order to increase the amount of weight lifted, even in raw lifting events. It's possible to see an overall increase in squats of from 5-25 pounds. Knee sleeves in general, especially when a knee sleeve is one or two sizes smaller than normal, can be very difficult to get the knee sleeve into proper position on the knee. Most powerlifters have very large calves in relation to their knees. This is due to the large amount of weight training performed. Further, most powerlifters have very large quadriceps which also make it difficult to pull a smaller knee sleeve up onto the upper leg.

In general knee sleeves are going to be used in raw lifting if they are no longer than 30 cm (11.81 inches) and more than 7 mm (0.28 inches) thick. They won't be able to touch the singlet and most of the time you are going to find a list of allowed sleeves.

Knee sleeves are designed to be extremely tight to prevent injury to the knee and adjoining muscles. This makes it very difficult to move the sleeve over the calf muscle and knee, especially since the calf muscle of most lifters/powerlifters is quite large compared to the size of the knee.

Knee sleeves can be expensive ranging in price between $4 to $300. For women, the pulling on of knee sleeves to get them over the calf and on the knee can result in broken nails, which can be costly for a woman who routinely gets her nails done. Constant pulling with large force on a knee sleeve can cause them to be overstretched, fatigued and torn at the seams or other locations, thus reducing the structural integrity of the knee sleeve.

Therefore, what is needed is a device which allows for ease of pulling a sleeve, such as a compression sleeve, over or onto an appendage of the human body.

What is further needed is a device which allows for ease of pulling a knee sleeve over the calf and the knee where the design of the knee sleeve remains unaltered during use of the device while pulling the sleeve over the calf and the knee.

What is still further needed is a method for using a device to allow for ease in applying a sleeve to an elbow or knee, or other part of the body that could benefit from a compression sleeve.

SUMMARY

Therefore, it is a primary object, feature, or advantage of the present disclosure to improve over the state of the art.

It is a further object, feature, or advantage of the present disclosure to make it easier for a user of a knee or elbow sleeve to pull the sleeve into position.

It is a still further object, feature, or advantage of the present disclosure to allow a user to move a knee sleeve into position quickly and easily and remain within the equipment rules of the powerlifting governing bodies.

Another object, feature, or advantage is to make application of a knee or elbow sleeve easier for handicapped people or those having only one arm.

Yet another object, feature, or advantage is reducing wear and tear on a knee or elbow sleeve due to constant tugging on the sleeve material.

A sleeve applicator in embodiments of the present disclosure may have one or more of the following features: (a) a sleeve applicator body, having (i) a front face, (ii) a right face, (iii) a left face, (iv) a rear face, (b) upper strap receptors extending from the front face to the rear face, and (c) lower strap receptors extending from the front face to the rear face, (d) an upper strap forming a closed loop and extending through the upper strap receptors, (e) a lower strap forming a closed loop and extending through the lower strap receptors, (f) a front raised face located on the front face, and (g) a top portion located between the right and the left face.

An apparatus for applying a sleeve in embodiments of the present disclosure may have one or more of the following features: (a) a first sleeve applicator body for placement between the sleeve and a user's body, (b) an upper strap extending from upper strap receptors located at an upper portion of the first sleeve applicator body, (c) a lower strap extending from lower strap receptors located at a lower portion of the first sleeve applicator body, (d) a second sleeve applicator body for placement between the sleeve and the user's body, (e) an upper strap extending from upper strap receptors located at an upper portion of the second sleeve applicator body, and (f) a lower strap extending from lower strap receptors located at a lower portion of the second sleeve applicator body.

An apparatus for applying a sleeve over a joint of a user in embodiments of the present disclosure may have one or more of the following features: (a) a first sleeve applicator for placement between the sleeve and user's body, the first sleeve applicator having, (i) a first strap operably coupled to an upper portion of the sleeve applicator, and (ii) a second strap operably coupled to the lower portion of the sleeve applicator, (b) a second sleeve applicator for placement between the sleeve and user's body, the second sleeve applicator located in opposing fashion to the first sleeve applicator and having, (i) a first strap operably coupled to an upper portion of the sleeve applicator, and (ii) a second strap operably coupled to the lower portion of the sleeve applicator.

One or more of these and/or other objects, features, or advantages of the present disclosure will become apparent from the specification and claims that follow. No single embodiment need provide every object, feature, or advantage. Different embodiments may have different objects, features, or advantages. Therefore, the present disclosure is not to be limited to or by any objects, features, or advantages stated herein.

BRIEF DESCRIPTION OF THE DRAWINGS

Illustrated embodiments of the disclosure are described in detail below with reference to the attached drawing figures, which are incorporated by reference herein.

Figure 1:
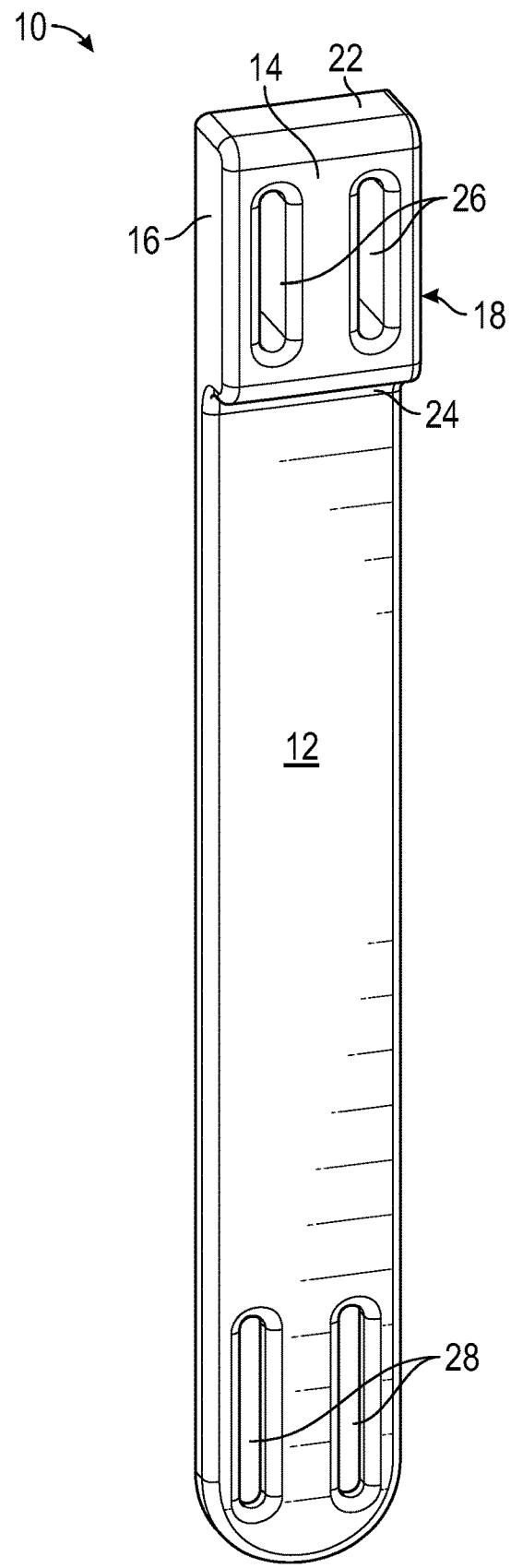
FIG. 1 is a front view of a sleeve applicator in an embodiment of the present invention.

Some of the figures include graphical and ornamental elements. It is to be understood the illustrative embodiments contemplate all permutations and combinations of the various graphical elements set forth in the figures thereof.

DETAILED DESCRIPTION

The following discussion is presented to enable a person skilled in the art to make and use the present teachings. Various modifications to the illustrated embodiments will be clear to those skilled in the art, and the generic principles herein may be applied to other embodiments and applications without departing from the present teachings. Thus, the present teachings are not intended to be limited to embodiments shown but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings. While embodiments of the present disclosure are discussed in terms of knee sleeves, it is fully contemplated embodiments of the present disclosure could be used in any sleeve application without departing from the spirit of the invention.

Embodiments of the present disclosure assist users in putting on knee sleeves, commonly used in powerlifting, and more generally, lifting, and in some instances compression sleeves for human appendages. Knee sleeves are designed to be extremely tight to prevent injury to the knee and adjoining muscles. This makes it very difficult to move the sleeve over the calf muscle and knee, especially since the calf muscle of most lifters/powerlifters is quite large compared to the size of the knee. Embodiments of the present disclosure allow a user to grip and lift a sleeve over the calf and over the knee while keeping the sleeve from bunching up during the process.

Embodiments of the present disclosure include an elongated, generally thin, member, with holes on each opposing end for receiving a pair of looped straps. In use, a knee sleeve is positioned about a lower portion of an individual's calf or ankle. A first one of the elongated members is inserted between the calf and sleeve with the top holes generally above the top portion of the sleeve and bottom holes generally above the bottom portion of the sleeve thereby availing the user access to the top strap attached through the top holes and the bottom strap attached through the bottom holes. A second one of the elongated members is positioned opposite the first one on the opposite side of the calf. The top strap is looped through the bottom strap of the first elongated member. Similarly, the top strap is looped through the bottom strap of the second elongated member. Pulling up on the top strap of the first elongated member with one hand and while pulling up on the top strap of the second elongated member the sleeve is moved upward from the calf to cover the knee.

With reference to FIG. 1, a sleeve applicator is shown in an embodiment of the present invention. Sleeve applicator 10, as shown, is most commonly one of a pair of sleeve applicators 10. Sleeve applicator 10 is preferably made of a rigid material, which is able to be pressed between a user's body and a sleeve to overcome the pressure between the user's body and the sleeve so the sleeve applicator can be pressed from one open end of a sleeve to another. These rigid materials could include plastics, polymers, metal, wood or any other material providing the necessary stiffness to perform the task of the sleeve applicator 10.

Sleeve applicator 10 is shown with a front face 12, a front raised face 14, a right face 16, left face 18, rear face 20 and a step portion 24. Further, sleeve applicator 10 can have a top set of loop receptors 26 and a bottom set of loop receptors 28. Upper strap receptors 26 are commonly located on raised face 14. While lower strap receptors 28 are located on a lower portion of front face 12. As shown, right face 16 and left face 18 are approximately 8 inches in length and ⅛ inch in thickness at front face 12 and a thickness of ⅜ inch at the raised face 14. Top portion 22 has a 1-inch length and ⅜-inch thickness. Raised face 14 has a 1¼ inch length. Upper strap receptors 26 and lower strap receptors 28 are both one inch long and ⅛ inch thick. At least one key aspect of the disclosure is to provide enough stiffness in the sleeve applicator 10 between upper strap receptors 26 and lower strap receptors 28 to keep the receptors 26, 28 spaced apart during use of the sleeve applicator 10. Although dimensions are shown, these are for illustrative purposes and for providing exemplary proportions that are not to be deemed as limiting to the various embodiments disclosed and contemplated herein.

Figure 2:
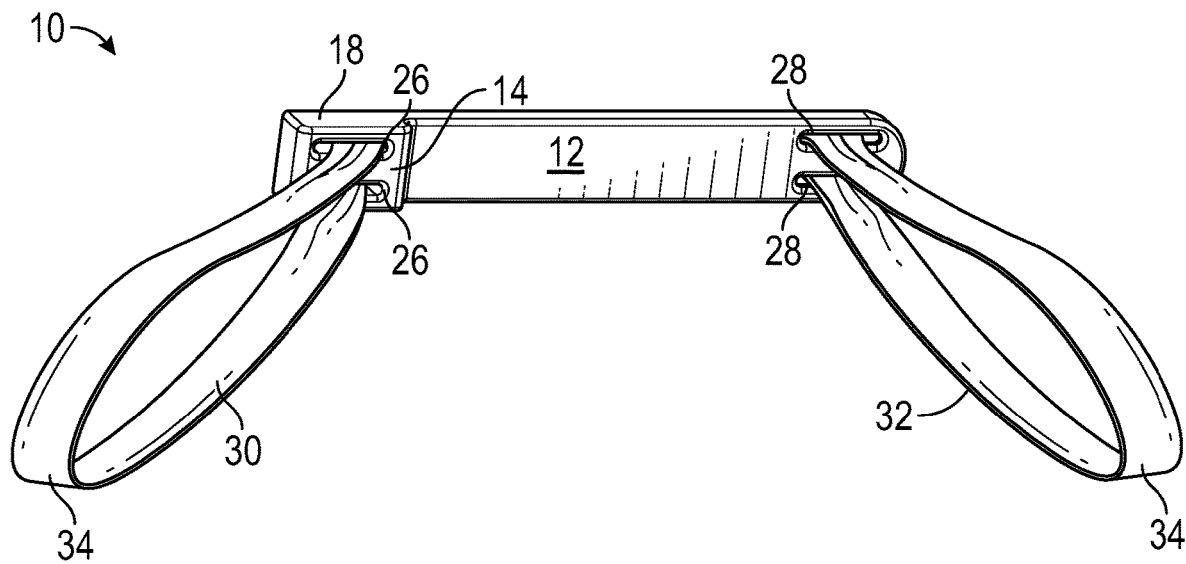
FIG. 2 is side view of a sleeve applicator with straps in an embodiment of the present invention.

With reference to FIG. 2, a sleeve applicator with straps is shown in an embodiment of the present invention. Upper strap 30 is shown being looped through upper strap receptors 26 and lower strap 32 is shown being looped through lower strap receptors 28. Upper strap 30 and lower strap 32 can be separate straps or a single strap looped through both receptors 26, 28.

Figure 3:
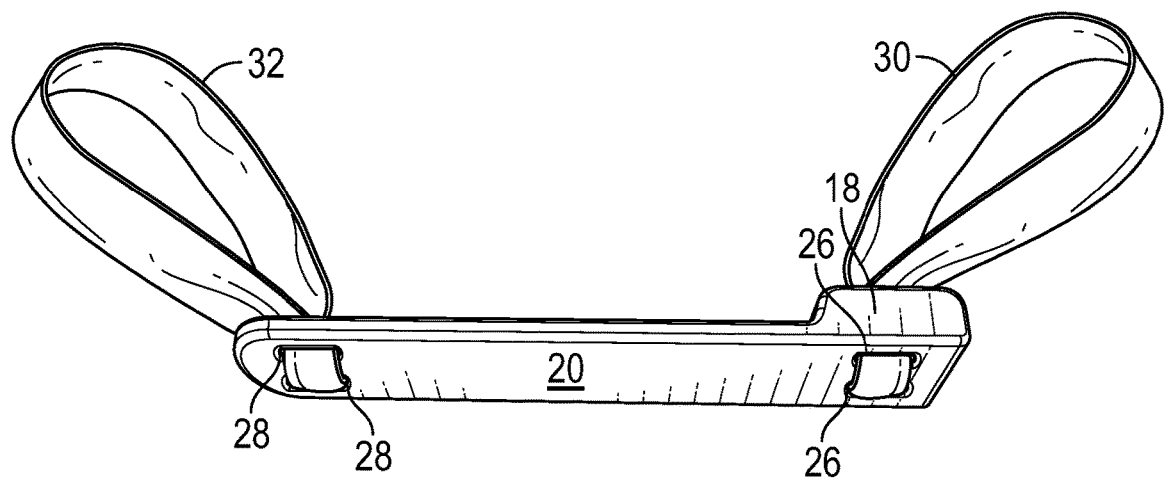
FIG. 3 is a rear view of a sleeve applicator with straps in an embodiment of the present invention

With reference to FIG. 3, a rear view of a sleeve applicator with straps is shown in an embodiment of the present invention. In the rear view, it is shown how upper strap 30 is threaded through an first aperture strap receptor 26 from the raised face 14 to rear face 20, then back through a second aperture of strap receptor 26 from the rear face 20 through to second aperture to the raised face 12. Both upper strap 30 and lower strap 32 are shown as having knots 34 on the straps; however, it is fully contemplated knots 34 can be replaced with ends of the straps 30, 32 being sown together, clipped together, stapled together, melted together or most any durable fashion of attachment without departing from the spirit of the invention. Lower strap 32 has a length, when fastened together to create a loop, generally equal to the distance of separation between the strap receptors 26, 28.

Sleeve applicator 10 can be configured with one or more labels or indicators for correctly positioning the sleeve applicator relative to the body. For example, the top set of loop receptors 26 can include printed, stamped, embossed, or sticker indicia, such as "UP", "TOP", or "TOPSIDE", and the bottom set of loop receptors 28 can include printed, stamped, embossed, or sticker indicia, such as, "DOWN", "BOTTOM", or "BOTTOMSIDE" to indicate how to position the sleeve applicator relative to the body. Additionally, such indicia can be configured to correspond with information provided, for example, on an instructions for use card, app, or webpage.

Figure 4:
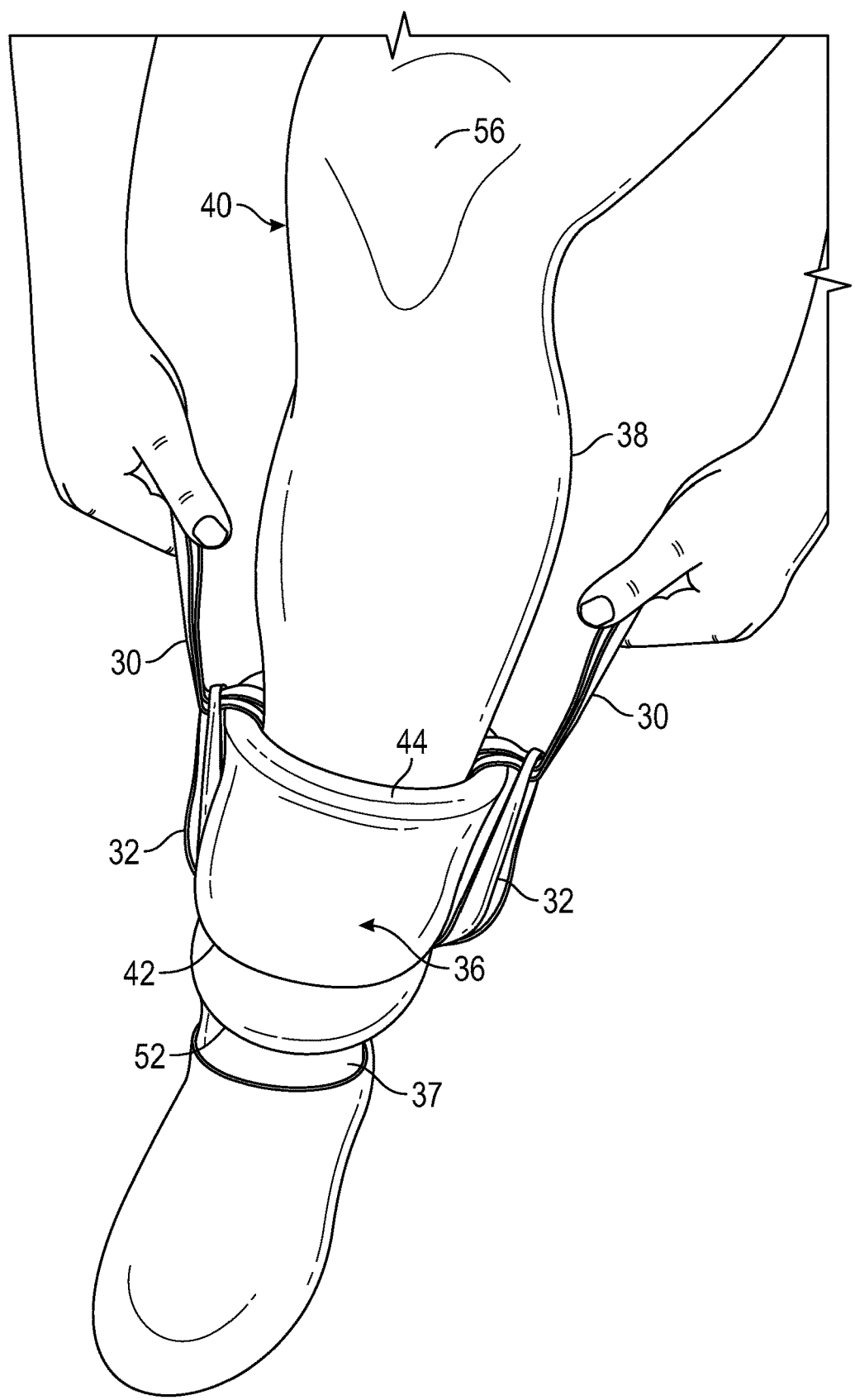
FIG. 4 is an elevated front view of a user prepping a sleeve applicator to be applied on a knee of a user in an embodiment of the present invention.

With reference to FIG. 4, an elevated front view of a user prepping a sleeve applicator to be applied on a knee of a user in an embodiment of the present invention is shown. By folding the sleeve 36 in half, the user 40 does not have to pull the sleeve up along the calf 38 before using the sleeve applicator 10. By folding the sleeve 36 in half, the user 40 need only get the sleeve 36 past their foot and over the ankle 37 just short of the calf 38.

A sleeve application process can be initialized, optionally, by first folding sleeve 36 approximately in half by rolling an upper portion 50 of sleeve 36 over a lower portion 52 of sleeve 36. The benefits to folding the sleeve in half are discussed in detail herein but folding of the sleeve is not required to properly apply the sleeve 36. Sleeve 36 can then be pulled over the user's foot and ankle until located just below the calf 37. User 40 would place their foot inside sleeve opening 54. Sleeve 36 is stopped short of the calf 38 as this can be the most difficult part of pulling up the sleeve. For user's with very large calves 38 or even if the user 40 is utilizing a sleeve 36 one to two sizes smaller than normal, then pulling the sleeve 36 over the calf 38 will be difficult.

Figure 5:
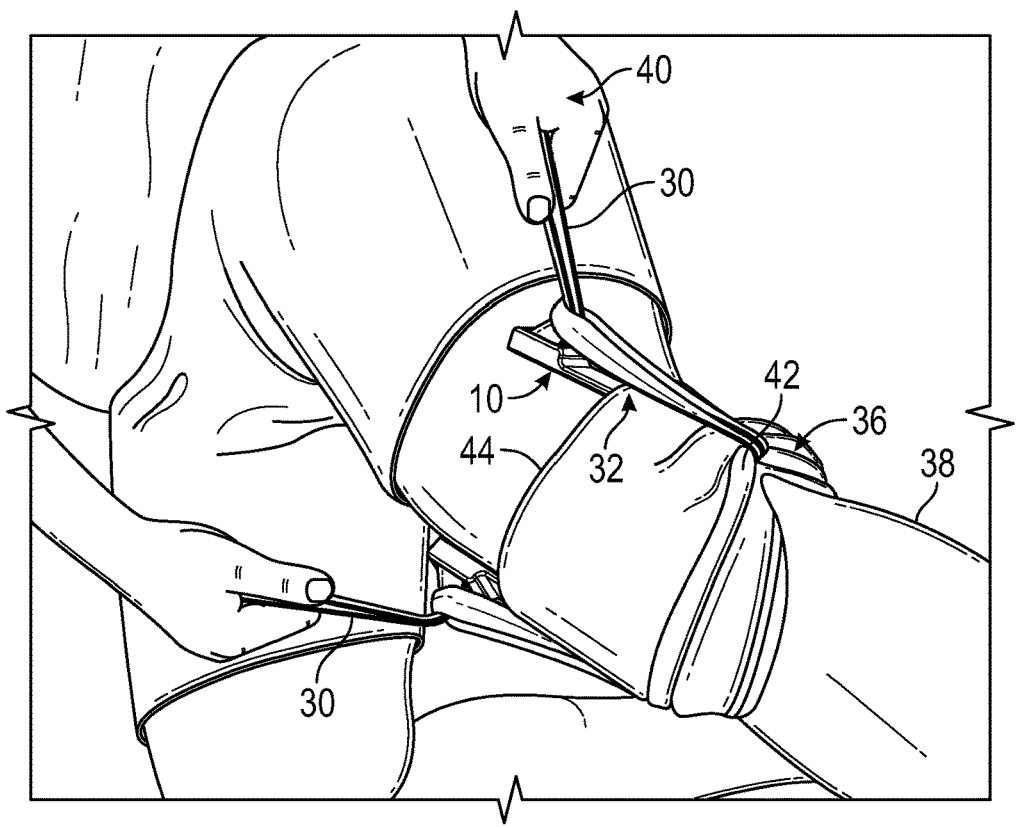
FIG. 5 is an elevated view of a user applying a knee sleeve with a pair of sleeve applicators in an embodiment of the present invention.
Figure 6:
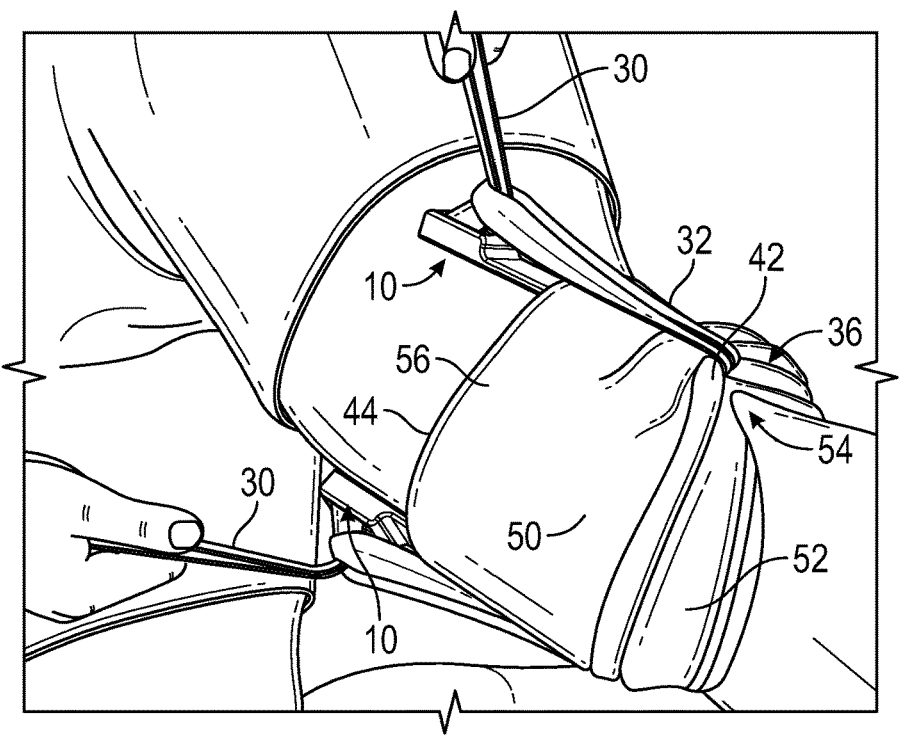
FIG. 6 is an exploded view of FIG. 4 in an embodiment of the present invention.

User 40 can insert a sleeve applicator 10 on the left or right side of ankle 37 through fold line 44, if sleeve 36 is folded, or upper portion 50 of sleeve 36 if the sleeve 36 is not folded. User 40 will push sleeve applicator 10 between the user's skin and sleeve 36 until the bottom set of loop receptors 28 appear from under the lower portion 52 of sleeve 36, or at least to where the lower strap 32 is accessible. User 40 will be able to grab the lower strap 32 and pull it through sleeve 36. The process is repeated for a sleeve applicator 10 on the opposite side of ankle 37. As for placement of each sleeve applicator, it can be beneficial to position each one slightly rearward of a midway point between the back of the calf and chin, or along the side where the calf muscle is largest. The upper strap 30 is routed through the lower strap 32 and pulled upward towards the user's head to secure the lower strap 32 in connection with upper strap 30 (as shown in FIGS. 4, 5 and 6). This is repeated for both sleeve applicators 10 on each side of ankle 37 or the elbow. User 40 would place their right hand through upper strap 30 and secure the upper strap 30 around the wrist (or the user 40 could pull with their fingers as shown in FIGS. 4 and 5). The user would then place their left hand through the opposite side upper strap 30 and secure the upper strap around the wrist. User 40 would then pull on the upper straps 30 with enough force to pull the sleeve applicators 10, and thus the sleeve 36, up over the user's joint; be it the knee 56, the elbow, or other portions of an appendage. User 40 would repeat this process for the other knee 56 or elbow if necessary.

With reference to FIG. 5, an elevated view of a user applying a knee sleeve with a pair of sleeve applicators in an embodiment of the present disclosure is shown. Knee sleeve 36 is shown as having been pulled over the user's calf 38 and partially onto the user's knee 56. As shown, user 40 is pulling on upper strap 30. Upper strap 30 has been looped through lower strap 32. Thus, when user 40 pulls on upper strap 30 the force of the pull is transferred from the upper strap 30 to the upper strap receptors 26 of the sleeve applicator 10. With the lifting of upper strap 30, lower strap 32 pulls knee sleeve 36 tight against the front face 12 of sleeve applicator 10 thereby opposing the tendency of the knee sleeve 36 to want to bunch up while being lifted. The lifting load is then carried by the sleeve applicator 10 and lower strap 32 with the lifting force being applied by a user at the upper strap 30.

During lifting and movement, sleeve applicator 10, located between the skin of the user 40 and the sleeve 36, slides along the user's skin while the sleeve 36 begins to bunch as indicated at 42. It is noted, the user 40 typically will begin with sleeve 36 folded in half. It should be noted that the sleeve 36 does not necessarily need to be folded in half, but there are benefits to folding the sleeve in half. For example, in addition to other reasons and explanations set forth herein, folding the sleeve in half decreases the area of sleeve material touching the skin and thereby reducing drag. Folding the sleeve in half also helps stiffen the sleeve which prevents it from bunching up as much as it would if applied unfolded.

First, the sleeve 36 can be up to 30 cm (11.8 inches) and this is longer than the 8-inch-long dimension shown in FIG. 1. Thus, by folding sleeve 36 in half to roughly 15 cm (5.9 inches) sleeve applicator 10 will extend above and below the sleeve 36 when pushed between the user's calf 38 and sleeve 36. This causes the sleeve applicator 10 to move along a substantially straight line along the user's leg.

Second, by folding the sleeve 36 in half, the user 40 does not have to pull the sleeve up along the calf 38 before using the sleeve applicator 10. By folding the sleeve 36 in half, the user 40 need only get the sleeve 36 past their foot and over the ankle just short of the calf 38.

Third, by folding the sleeve 36 in half, the user 40 does not have to bunch up the sleeve 36 in order to extend the 8-inch sleeve applicator 10 through the 30 cm sleeve 36. It is also of note, raised face 14 with a step portion 24 catches the fold line 44 of the sleeve 36 assisting in not allowing the sleeve 36 to pull up over the raised face 14 of sleeve applicator 10.

With reference to FIG. 6, an exploded view of FIG. 4B in an embodiment of the present disclosure is shown. In FIG. 5, the user 40 is using one to two fingers to grasp around upper strap 30; however, the present disclosure contemplates that upper strap 30 is wide enough the user could stick their entire hand within upper strap 30 and thus pull with their wrists instead of just a few fingers. Thus, user 40 would have much greater pulling force to pull sleeve 36 up over their knee 56.

Figure 7:
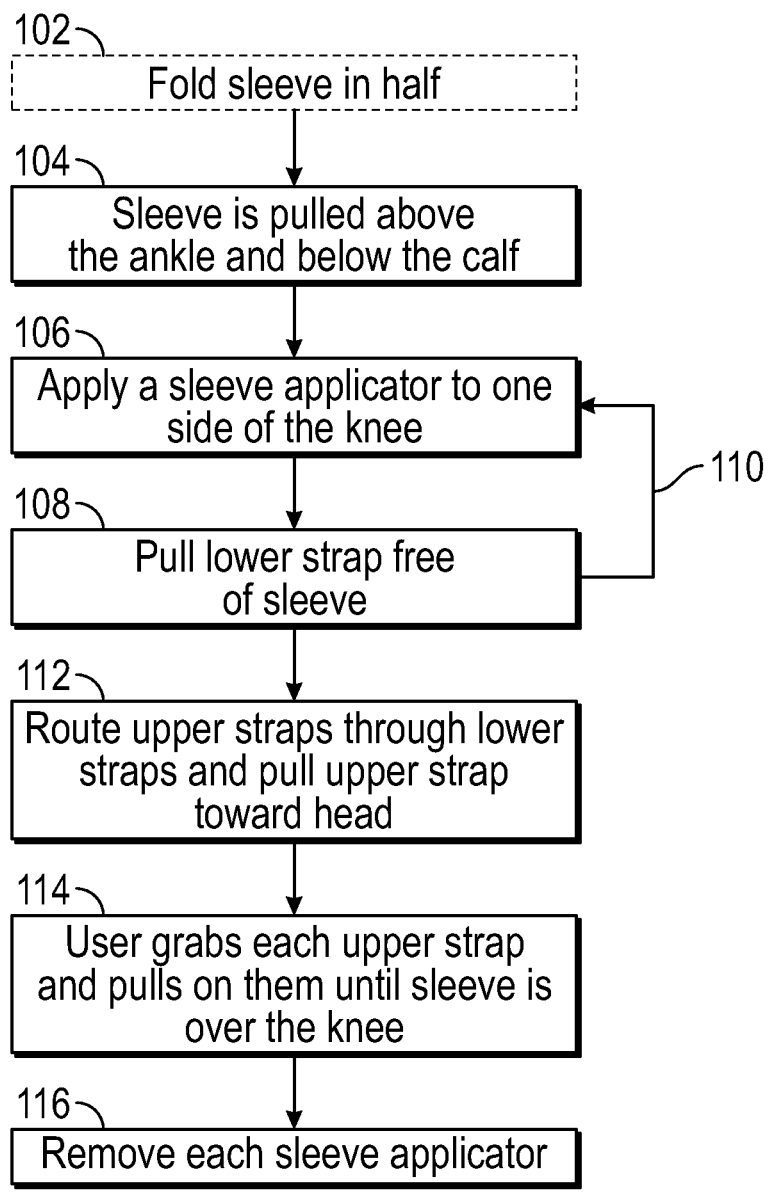
FIG. 7 is a flowchart diagram of a method of application of an athletic sleeve over a knee or elbow in an embodiment of the present invention.

With reference to FIG. 7, a flowchart diagram of a method of application of an athletic sleeve over a knee or elbow is show in an embodiment of the present invention. This same method of applying a knee or elbow sleeve can be used to apply various types of compression sleeves to appendages of the body, especially where help or assistance with applying a sleeve is desired. A sleeve application process 100 can be initialized, optionally, at state 102 by first folding sleeve 36 approximately in half by rolling an upper portion 50 of sleeve 36 over a lower portion 52 of sleeve 36. The benefits to folding the sleeve in half are discussed in detail herein but folding of the sleeve is not required to properly apply the sleeve 36. Sleeve 36 can then be pulled over the user's foot and ankle until located just below the calf at state 104. User 40 would place their foot inside sleeve opening 54. Sleeve 36 is stopped short of the calf 38 as this can be the most difficult part of pulling up the sleeve. For user's with very large calves 38 or even if the user 40 is utilizing a sleeve 36 one to two sizes smaller than normal, then pulling the sleeve 36 over the calf 38 will be difficult.

At state 106, user 40 can insert a sleeve applicator 10 on the left or right side of knee 56 through fold line 44, if sleeve 36 is folded, or upper portion 50 of sleeve 36 if the sleeve 36 is not folded. User 40 will push sleeve applicator 10 between the user's skin and sleeve 36 until the bottom set of loop receptors 28 appear from under the lower portion 52 of sleeve 36, or at least to where the lower strap 32 is accessible. At state 108, user 40 will be able to grab the lower strap 32 and pull it through sleeve 36. At state 110, the process of state 106 and 108 are repeated for a sleeve applicator 10 on the opposite side of knee 56. As for placement of each sleeve applicator, it can be beneficial to position each one slightly rearward of a midway point between the back of the calf and chin, or along the side where the calf muscle is largest. At state 112, the upper strap 30 is routed through the lower strap 32 and pulled upward towards the user's head to secure the lower strap 32 in connection with upper strap 30 (as shown in FIGS. 4A, 4B and 5). Step 112 is repeated for both sleeve applicators 10 on each side of knee 56 or the elbow. At state 114, user 40 would place their right hand through upper strap 30 and secure the upper strap around the wrist (or the user 40 could pull with their fingers as shown in FIGS. 4 and 5). The user would then place their left hand through the opposite side upper strap 30 and secure the upper strap around the wrist. User 40 would then pull on the upper straps with enough force to pull the sleeve applicators 10, and thus the sleeve 36, up over the user's joint; be it the knee, the elbow, or other portions of an appendage. User 40 would repeat this process for the other knee 56 or elbow if necessary.

It's of note, should the sleeve applicators be used by a user 40 with only one arm, an attachment in the form of a cylinder or brace could be looped through each of the upper straps 30, thus creating a handle allowing the user to pull with their one hand. It is also contemplated that this cylinder or brace could also be attached by a tether to a mouthguard where user 40 could pull up the knee sleeves with their head should they have the inability to pull with their arms. Finally, at state 116, user 40 can utilize the sleeves 36 and workout, lift weights or for whatever purpose the user intended to wear the sleeve 36.

Figure 8:
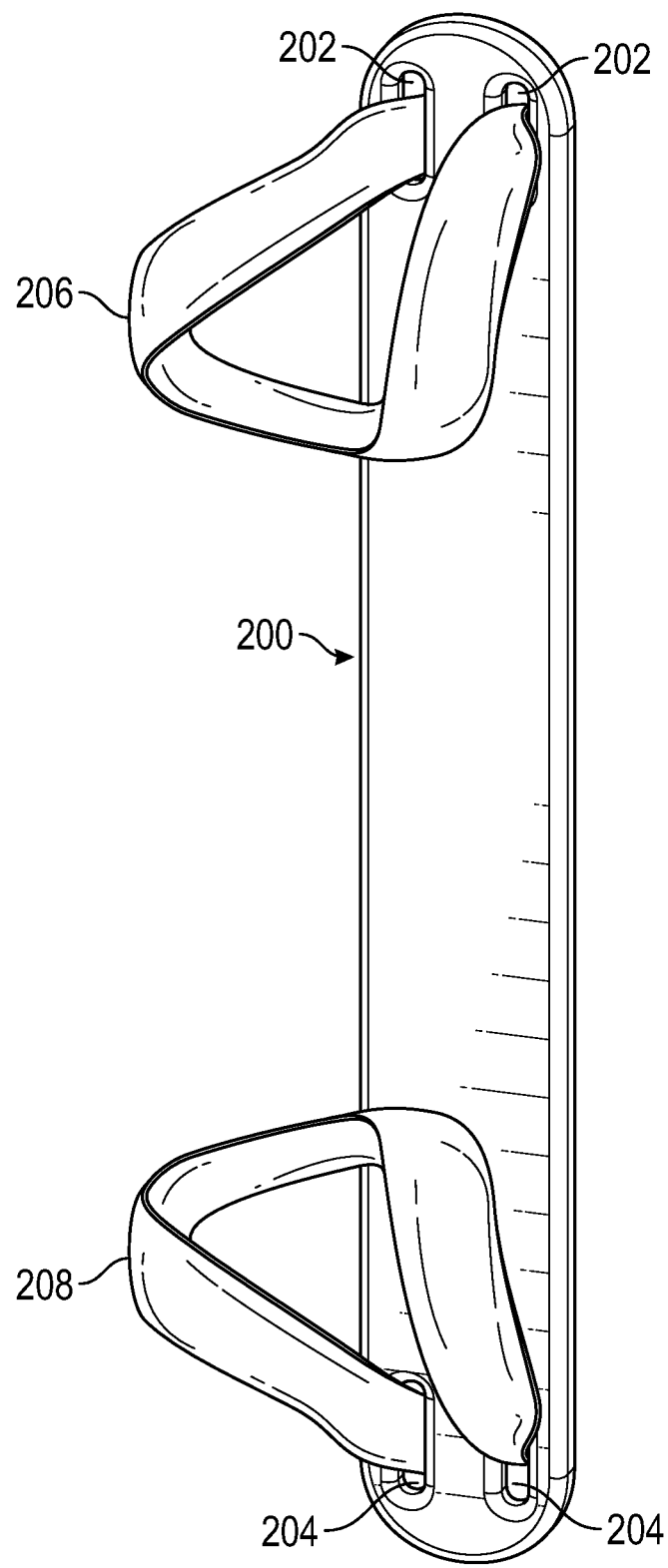
FIG. 8 is a front profile view of another sleeve applicator in an embodiment of the present invention.
Figure 9:
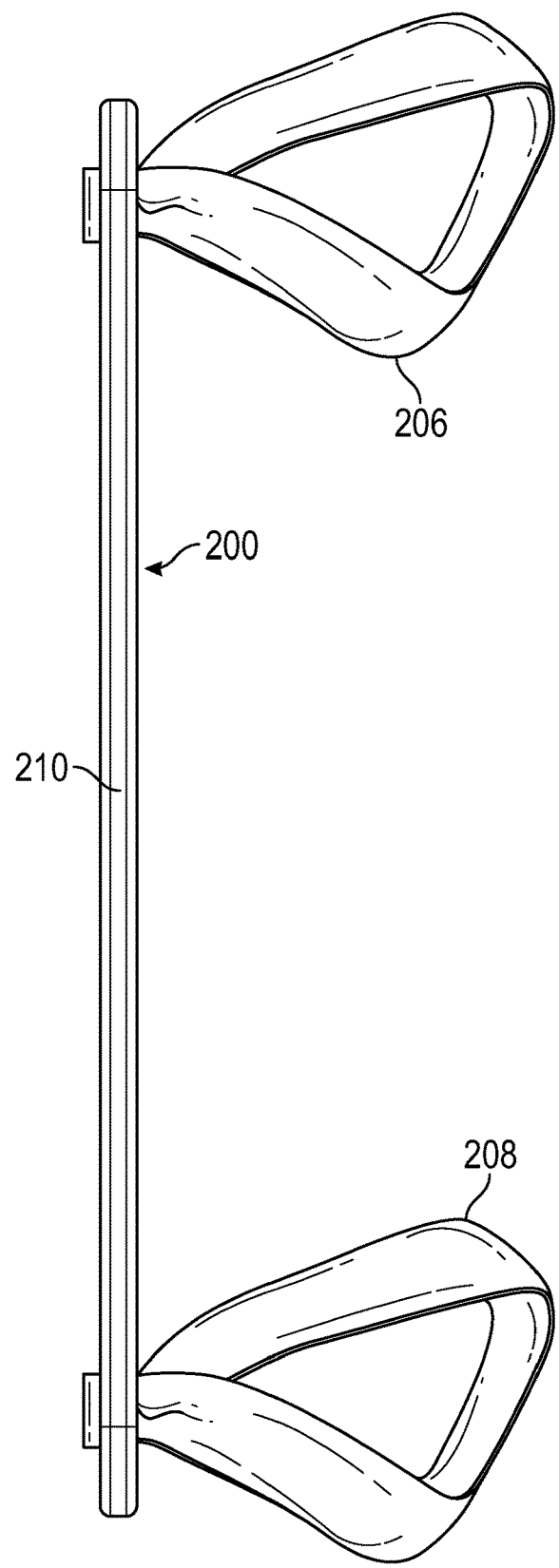
FIG. 9 is a side profile view of another sleeve applicator in an embodiment of the present invention.

With reference to FIGS. 8 & 9, a front and side profile view of another sleeve applicator in an embodiment of the present disclosure is shown. Sleeve applicator 200 has upper set of loop receptors 202 and lower set of loop receptors 204 along with upper strap 206 and lower strap 208. A uniform and thinner body 210 is shown in FIG. 8. A thinner body 210 can make the application step at 106 easier as the body is thinner and can fit between the user's body and sleeve 36 much easier even with tight tolerances.

Figure 10:
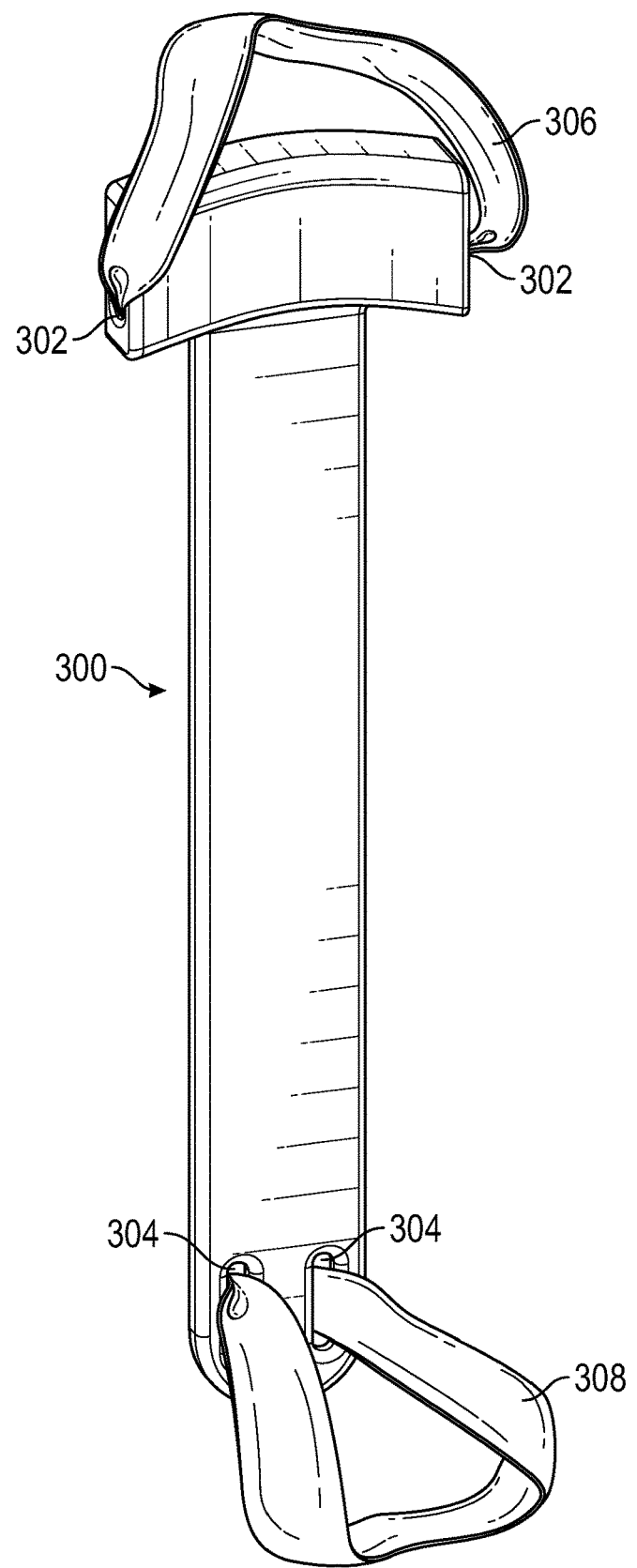
FIG. 10 is a front profile view of another sleeve applicator in an embodiment of the present invention.
Figure 11:
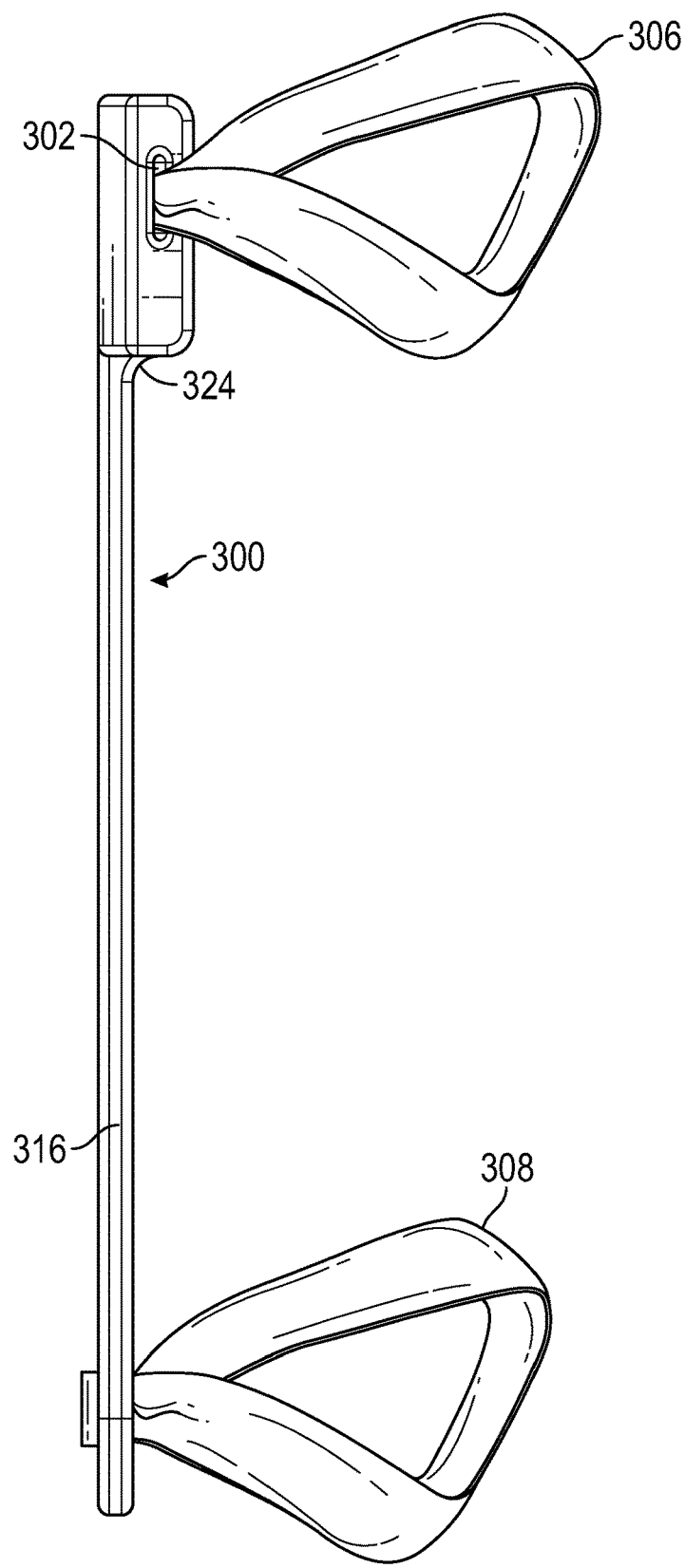
FIG. 11 is a side profile view of another sleeve applicator in an embodiment of the present invention.

With reference to FIGS. 10 & 11, a front and side profile view of another sleeve applicator in an embodiment of the present disclosure is shown. Sleeve applicator 300 has upper set of loop receptors 302 and lower set of loop receptors 304 along with upper strap 306 and lower strap 308. Sleeve applicator 300 has a similar body to sleeve applicator 10 when observed from a profile view, such as FIG. 10. A similar beveled face 324 can be seen, but the upper set of loop receptors 302 are located on the side 316 of sleeve applicator 300. Providing the upper set of loop receptors 302 on the side 316 of sleeve applicator more of a direct upward force on sleeve applicator 300 and reduce the tangential force applied in an outward fashion when the upper set of loop receptors are located on the raised face 14 on sleeve applicator 10.

Figure 12:
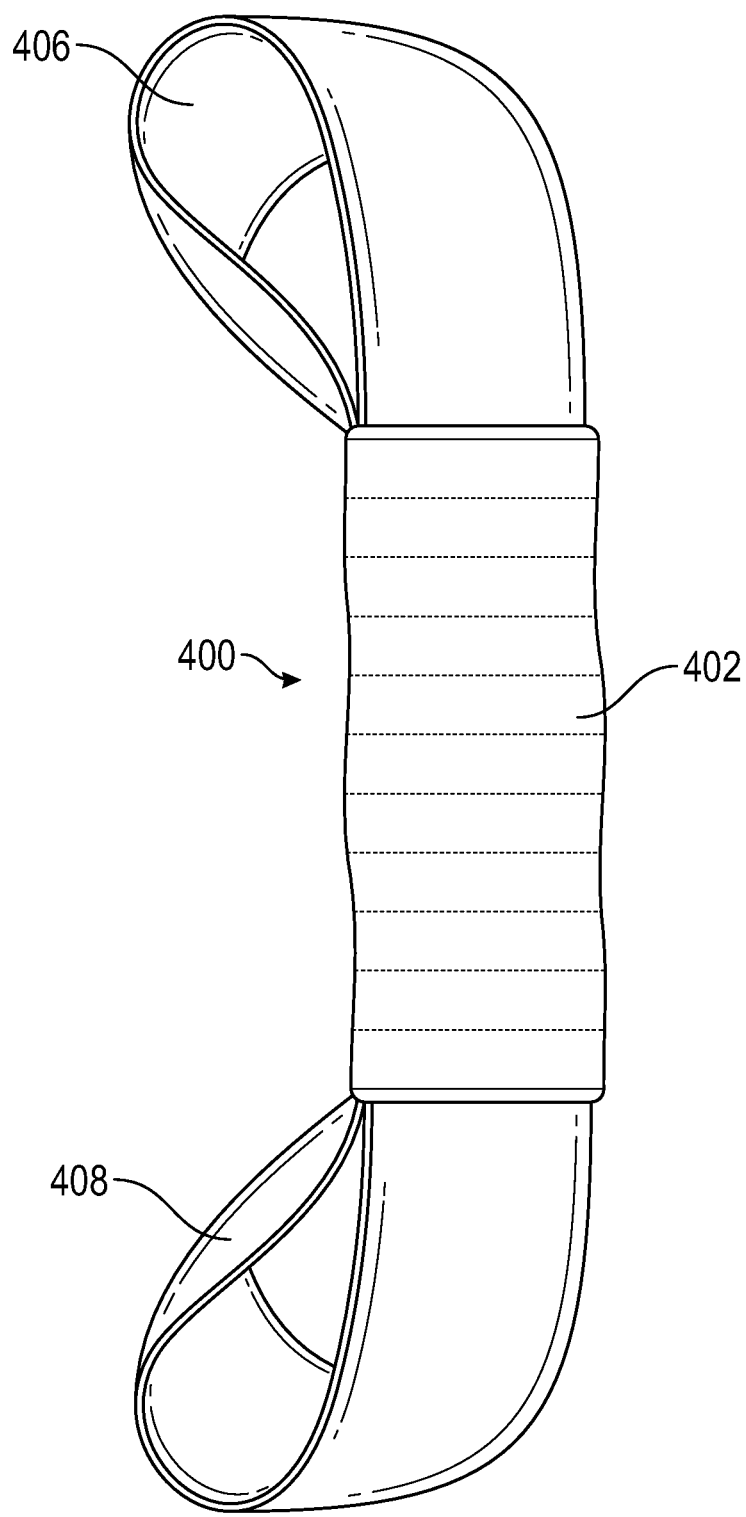
FIG. 12 is a front/side profile view of another sleeve applicator in an embodiment of the present invention.
Figure 13:
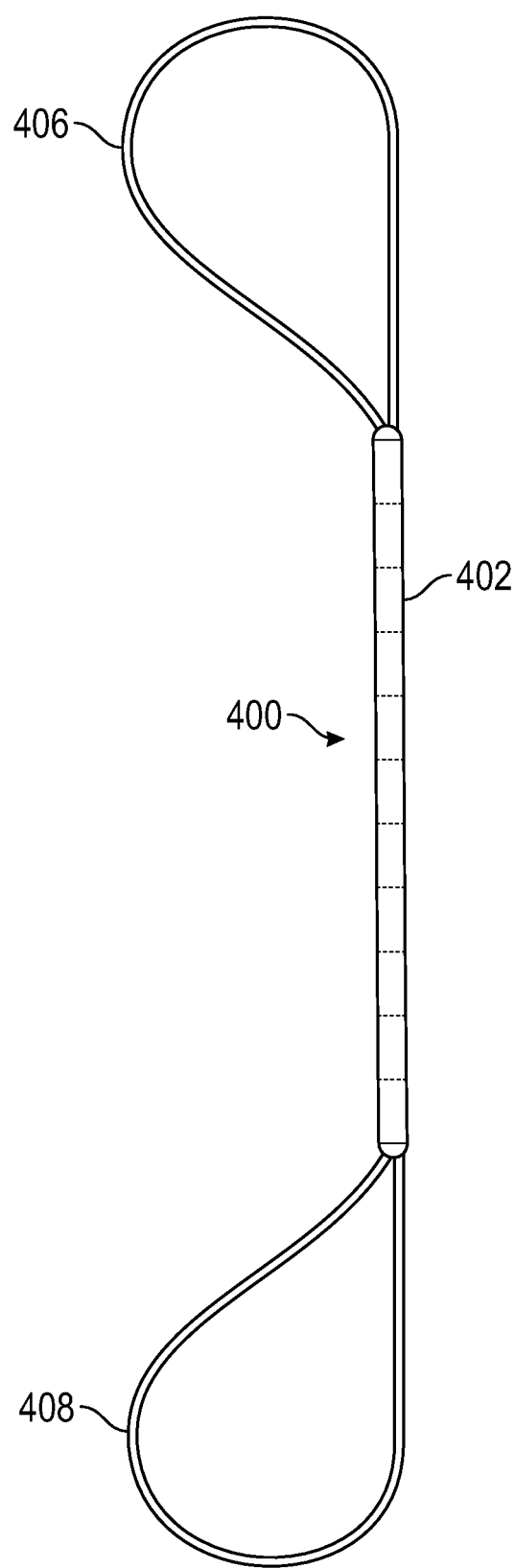
FIG. 13 is a side profile view of another sleeve applicator in an embodiment of the present invention.

With reference to FIGS. 12 & 13, a front/side and side profile view of another sleeve applicator in an embodiment of the present disclosure is shown. Sleeve applicator 400 has no set of loop receptors, but instead the upper strap 406 and lower strap 408 are all part of the main body 402. Sleeve applicator 400 has a main body 402 which can be made from a thick and rigid fabric, such as a heavy-duty Nylon, multiple layer burlap and Kevlar. This material would allow sleeve applicator 400 to be inserted between the user and the sleeve applicator 400 and be pushed to the sleeve lower portion 52 from the upper portion 50 without bunching up, but instead remaining rigid. Furthermore, sleeve applicator 400 is a one-piece unit, making it easy to manufacture and package and reduce labor costs in manufacturing.

Figure 14:
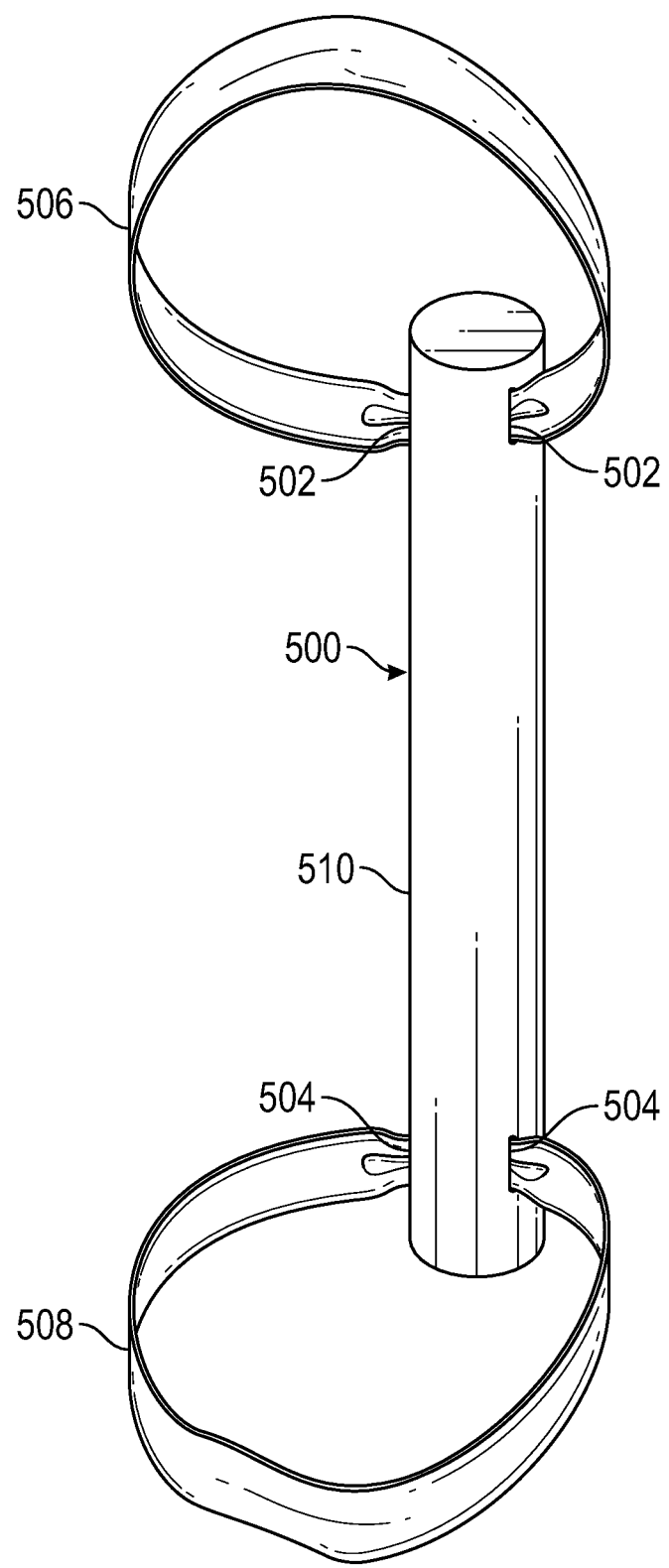
FIG. 14 is a front/side profile view of another sleeve applicator in an embodiment of the present invention.
Figure 15:
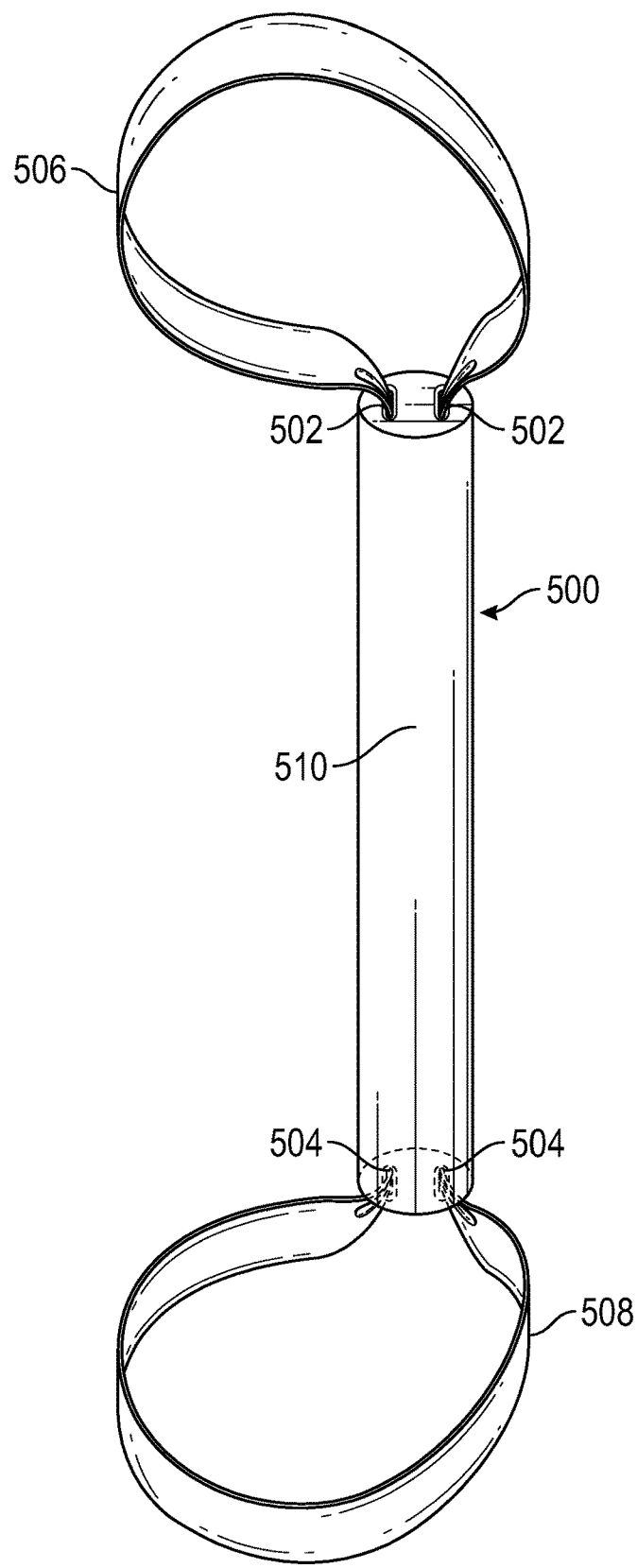
FIG. 15 is a side profile view of another sleeve applicator in an embodiment of the present invention.

With reference to FIGS. 14 & 15, a front and side profile view of another sleeve applicator in an embodiment of the present disclosure is shown. Sleeve applicator 500 has upper set of loop receptors 502 and lower set of loop receptors 504 along with upper strap 506 and lower strap 508. Sleeve applicator 500 has a body 510 which is cylinder in shape. A cylinder shape can reduce the amount of surface area exposed to the friction of the user's skin and the sleeve 36 itself. By lowering the friction coefficient, it is easier for user 40 to push sleeve applicator 500 between the user and the sleeve 36 during process 100. The application further contemplates the possibility of the user 40 being able to insert one strap through the body 510 and for body 510 not needing any loop receptors 502, 504. Thus, in operation, the user could extend cylinder body 510 through between the user's skin and sleeve 36. Then the user 40 could route one strap from the upper opening, through the cylinder to the lower opening, thus creating an upper strap 506 and a lower strap 508 out of a single strap.

Figure 16:
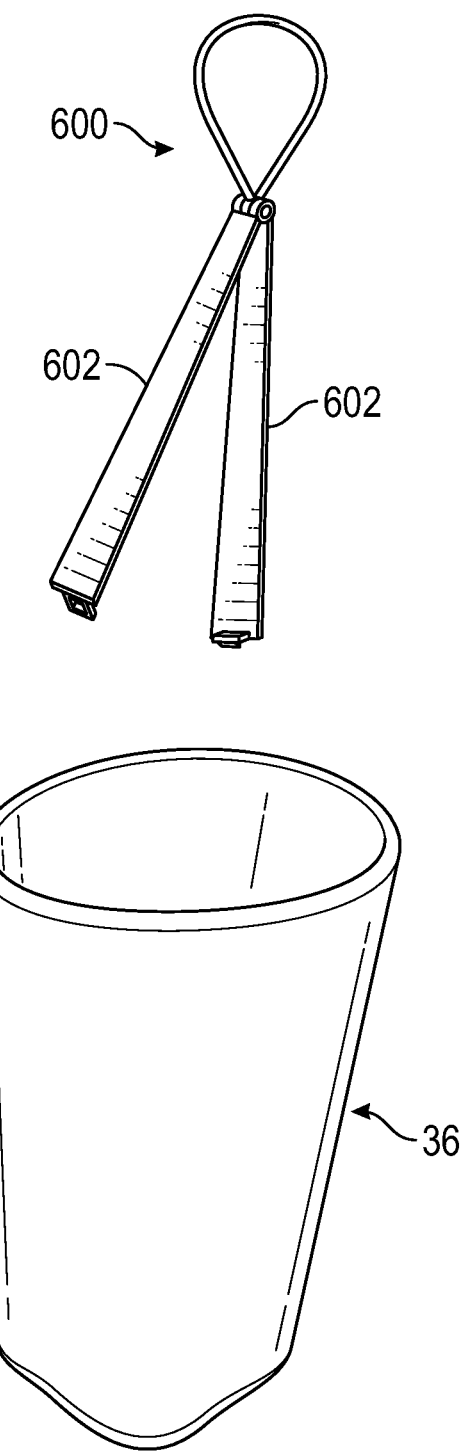
FIG. 16 is a front profile view of another sleeve applicator in an embodiment of the present invention.

With reference to FIG. 16, a front profile view of another embodiment of a sleeve applicator is shown in an embodiment of the present invention. Sleeve applicator 600 is shown in a compressed spring form. In use, the user 40 would squeeze the applicator 600, which would open extension arms 602 (e.g., push extension arms away from each other). The user 40 would then place one extension arm 602 on the inside of sleeve 36 and the other extension arm 602 on the outside of sleeve 36. The user would then release the applicator 600 and extension arms 602 would close thus pinching the sleeve 36 in between them. Enough force is created between the extension arms 602 to allow the user 40 to pull on applicator 600 and thus pull up sleeve applicator over the user's knee 56 or elbow. After the sleeve 36 was pulled over knee 56, the user 40 could squeeze the applicator 600 once again to push extension arms 602 away from each other and release the sleeve 36. The user 40 would then pull the sleeve applicator 600 away from the sleeve 36.

The disclosure is not to be limited to the embodiments described herein. In particular, the disclosure contemplates numerous variations in sleeve application. The foregoing description has been presented for purposes of illustration and description. It is not intended to be an exhaustive list or limit any of the disclosure to the precise forms disclosed. It is contemplated that other alternatives or exemplary aspects are considered included in the invention. The description is merely examples of embodiments, processes or methods of the invention. It is understood that any other modifications, substitutions, and/or additions can be made, which are within the intended spirit and scope of the invention.

What is claimed is:

1. An apparatus for applying a sleeve, comprising:
   a first sleeve applicator body for placement between the sleeve and a user's body;
   an upper strap extending from upper strap receptors located at an upper portion of the first sleeve applicator body; and
   a lower strap extending from lower strap receptors located at a lower portion of the first sleeve applicator body;
   wherein the upper strap is placed within the lower strap and pulled toward the user to connect the upper and the lower strap together.

2. The apparatus of claim 1 further comprising:
   a second sleeve applicator body for placement between the sleeve and the user's body.

3. The apparatus of claim 2, further comprising:
   an upper strap extending from upper strap receptors located at an upper portion of the second sleeve applicator body; and
   a lower strap extending from lower strap receptors located at a lower portion of the second sleeve applicator body.

4. The apparatus of claim 3, wherein the first and second sleeve applicator are located on opposing sides of a sleeve during operation of the first and second sleeve applicators.

5. The apparatus of claim 4, wherein the sleeve is a knee sleeve.

6. An apparatus for applying a sleeve over a joint of a user, comprising:
   a first sleeve applicator for placement between the sleeve and user's body, the first sleeve applicator having:
      a first strap operably coupled to an upper portion of the sleeve applicator; and
      a second strap operably coupled to the lower portion of the sleeve applicator; and
   a second sleeve applicator for placement between the sleeve and user's body, the second sleeve applicator located in opposing fashion to the first sleeve applicator and having:
      a first strap operably coupled to an upper portion of the sleeve applicator; and
      a second strap operably coupled to the lower portion of the sleeve applicator;
   wherein the first and the second applicator are removed once the sleeve is properly placed over the user's joint.

7. The apparatus of claim 6, wherein the sleeve can be folded or unfolded during application.

8. The apparatus of claim 6, wherein the first and second sleeve applicators are pushed between the sleeve and the user's body until the second strap of the first and second sleeve applicator extends out of a bottom of the sleeve.

9. The apparatus of claim 8, wherein the first strap of the first and second sleeve applicators is capable of being pulled through the second strap and then pulled away from the second strap for locking the first and the second strap together in a working relationship.

10. The apparatus of claim 9, wherein the user can place at least one finger within the upper strap in order to pull upon the upper strap.

11. The apparatus of claim 10, wherein the user can place their entire hand within the upper strap and pull with their wrist.

* * * * *